(12) United States Patent
Nekovar et al.

(10) Patent No.: US 7,580,503 B2
(45) Date of Patent: Aug. 25, 2009

(54) DIAGNOSTICS DEVICE COMPRISING AN X-RAY SYSTEM WITH COORDINATED FREQUENCY OPERATION

(75) Inventors: Anton Nekovar, Neunkirchen (DE); Bernhard Sandkamp, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 559 days.

(21) Appl. No.: 11/387,996

(22) Filed: Mar. 23, 2006

(65) Prior Publication Data
US 2006/0241372 A1    Oct. 26, 2006

(30) Foreign Application Priority Data
Mar. 24, 2005 (DE) .................... 10 2005 014 286

(51) Int. Cl.
*A61B 6/00* (2006.01)
*G01N 23/083* (2006.01)
(52) U.S. Cl. ..................... 378/42; 378/62; 600/429
(58) Field of Classification Search ............... 378/42, 378/62, 98.12, 114, 115, 116; 600/407, 425, 600/429
See application file for complete search history.

(56) References Cited

U.S. PATENT DOCUMENTS

| 5,038,369 | A | * | 8/1991 | Nishiki | 378/62 |
| 5,224,141 | A | * | 6/1993 | Yassa et al. | 378/98.2 |
| 5,251,635 | A | * | 10/1993 | Dumoulin et al. | 600/417 |
| 5,265,610 | A |   | 11/1993 | Darrow et al. | |
| 5,377,678 | A | * | 1/1995 | Dumoulin et al. | 600/424 |
| 5,752,513 | A |   | 5/1998 | Acker et al. | |
| 5,757,884 | A |   | 5/1998 | Alexandrescu | |
| 5,913,820 | A | * | 6/1999 | Bladen et al. | 600/407 |
| 6,823,207 | B1 | * | 11/2004 | Jensen et al. | 600/427 |
| 6,996,430 | B1 | * | 2/2006 | Gilboa et al. | 600/407 |
| 7,065,393 | B2 | * | 6/2006 | Sati et al. | 600/407 |
| 7,103,136 | B2 | * | 9/2006 | Claus et al. | 378/4 |
| 7,174,202 | B2 | * | 2/2007 | Bladen et al. | 600/424 |
| 7,236,567 | B2 | * | 6/2007 | Sandkamp et al. | 378/114 |

* cited by examiner

*Primary Examiner*—Allen C. Ho

(57) ABSTRACT

The invention relates to a diagnostics device and to a method for the operation thereof comprising an X-ray system for producing X-ray images, the system comprising an X-ray device and an image system for the X-ray device, and a system for locating objects, wherein adjusting means for changing the frequency of at least one of the two systems are provided, by way of which the two systems can be coordinated with one another such that interference within successive X-ray images is virtually static, and the image system comprises a correcting device which is constructed such that the static interference is eliminated. Diagnostics devices of this type are used in various medical procedures, for example in PCI (Percutaneous Coronary Intervention) and Cardiac EP (electrophysiology) interventions.

17 Claims, 2 Drawing Sheets

DIAGNOSTICS DEVICE COMPRISING AN X-RAY SYSTEM WITH COORDINATED FREQUENCY OPERATION

CROSS REFERENCE TO RELATED APPLICATIONS

This application claims priority to the German application No. 10 2005 014 286.9, filed Mar. 24, 2005 which is incorporated by reference herein in its entirety.

FIELD OF INVENTION

The invention relates to a diagnostics device comprising an X-ray system for producing X-ray images with an image frequency, the system comprising an X-ray device and an image system for the X-ray device, a system for locating objects with an operating frequency and a control device for the systems, as well as to a method for operating the diagnostics device comprising an X-ray system for producing image signals with an image frequency and a system for locating objects with an operating frequency, wherein, in the case of the locating systems, the amplitudes of the different magnetic fields are measured through the object and the positions of the object are determined therefrom. Diagnostics devices of this type are used in various medical procedures, for example in PCI (Percutaneous Coronary Intervention) and Cardiac EP (electrophysiology) interventions.

BACKGROUND OF INVENTION

An above-mentioned X-ray system with a flat image converter which comprises a scintillator layer and a semiconductor layer with pixel elements arranged in a matrix is known from U.S. Pat. No. 5,757,884. These so-called flat image detectors have only recently been introduced onto the market.

In the field of medical engineering there are catheter locating systems which work with magnetic or electromagnetic fields. U.S. Pat. No. 5,752,513 A describes a magnetic locating system for catheters of this type. In flat image detectors, as are increasingly used in X-ray engineering, these locating systems lead to image interference owing to their strong magnetic fields. This interference can, for example, be in the form of horizontal stripes in the image which are superimposed as additive components on the actual image information.

SUMMARY OF INVENTION

In the past image intensifiers with coupled CCD cameras were primarily used as the image converters. These image intensifiers and the CCD cameras are not affected by the fields irradiated by the locating system. Therefore this problem was not known before. However, flat image detectors are used virtually exclusively in the case of new X-ray systems.

A diagnostics device comprising an X-ray system for producing X-ray images, which system comprises an X-ray device with an X-ray image intensifier and an image system for the X-ray device, and with a system for locating objects is known in U.S. Pat. No. 5,265,610 A, with both the image frequencies of the X-ray system and the operating frequencies of the system for locating objects being able to amount to between 12 and 60 HZ.

The invention is based on the object of developing a diagnostics device of the type mentioned at the outset such that the image interference is much reduced or completely eliminated.

The object is achieved according to the invention in that
adjusting means for changing at least the image frequency or the operating frequency of the systems are provided, by way of which the systems can be coordinated with one another such that interference within successive X-ray images is virtually static, and
the image system comprises a correcting device which is constructed such that the static interference is eliminated.

Image artifacts that occur when using catheter locating systems in combination with X-ray systems can be completely eliminated as a result of this correction.

If a control device for at least one of the systems is provided in the diagnostics device, it can comprise the adjusting means for changing the frequency of at least one of the systems.

According to the invention, the correction device can comprise an image memory for a correction image, which, together with the following X-ray images, is supplied to a subtraction stage.

The adjusting means for changing the operating frequencies of the system ca n advantageously be constructed for locating objects.

It has proven to be advantageous if the image frequency of the X-ray system is 30 Hz, wherein the operating frequency of the device for locating objects can be a multiple of 30 Hz.

Alternatively, the adjusting means can change the image frequency of the X-ray system, wherein the image frequency of the X-ray system can be an integral divisor of the operating frequency of the system for locating objects.

In a system for locating objects with a plurality of operating frequencies, it has proven to be expedient if the adjusting means are constructed such that the difference in the operating frequencies of the system for locating objects is 200 Hz.

The object is achieved according to the invention for a method in that the frequencies of the two systems are coordinated with one another such that interference of the locating system is virtually static in the X-ray image within successive X-ray images, and in that the image signal is corrected in the sense of a minimization of static interference.

It has proven to be advantageous if a correction image is created and the subsequent exposed X-ray images are corrected therewith.

According to the invention, the correction image can be subtracted from the X-ray images following the correction image.

An integral multiple of the image frequency of the X-ray system can advantageously be selected as the operating frequency of the system for locating objects.

If the system for locating objects can be operated at a plurality of frequencies, it is recommended according to the invention to select an integral multiple of the operating frequency of the image system as the differences in the frequencies.

The correction image can advantageously be created at the beginning of an examination and be subtracted from all X-ray images of the examination. Alternatively, the correction image can be repeatedly created after an adjustable number of X-ray images and the current correction image subtracted from immediately following X-ray images.

BRIEF DESCRIPTION OF THE DRAWINGS

The invention is described in more detail hereinafter with reference to embodiments illustrated in the drawings, in which.

DETAILED DESCRIPTION OF THE DRAWINGS

Figure 1:
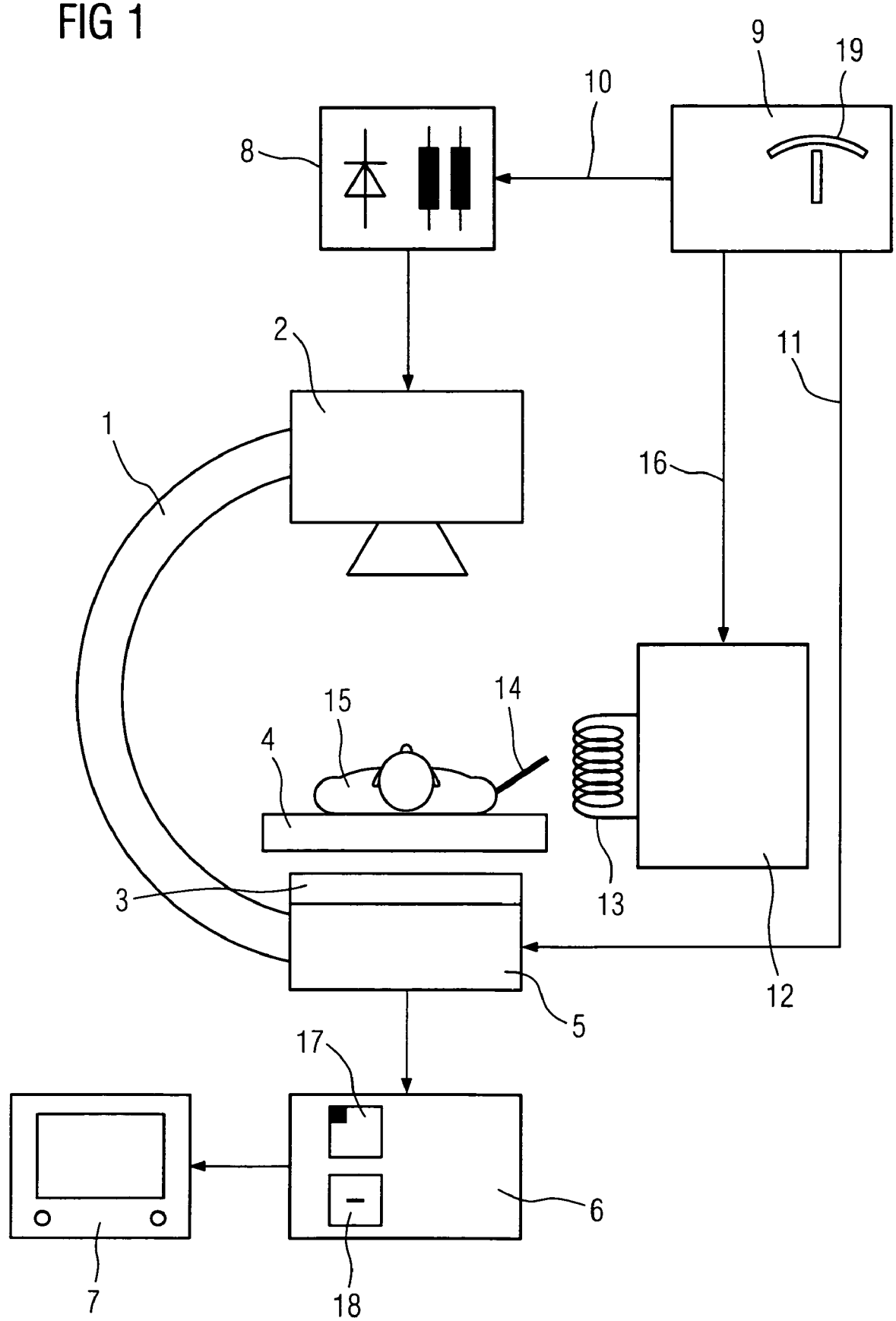
FIG. 1 shows a diagnostics device comprising X-ray system and locating system.

FIG. 1 shows a diagnostics device which comprises a C-arm 1 to which an X-ray emitter 2 and a flat image detector 3 are fastened. A patient 15, who is lying on a patient screening table 4 between X-ray emitter 2 and flat image detector 3, can be permeated with X-rays by means of this X-ray diagnostics device. The X-rays, which are attenuated by the patient, are detected by the flat image detector 3.

The support for the C-arm 1 of the X-ray diagnostics device is not shown. Any known support can be used which is either mounted on the floor or on the ceiling.

An electronic read-out device 5, which is known per se and which brings about a read-out of the image data, is associated with the flat image detector 3. This data is supplied to an X-ray image system 6 which converts the data into an image which is reproduced on a monitor 7.

A high voltage generator 8, which is operated by a control device 9 via a control line 10, is connected to the X-ray emitter 2. The control device 9 is connected via a control line 11 to the electronic read-out device 5 for the flat image detector 3.

The diagnostics device also comprises a magnetic locating system 12, for example for a catheter 14, which generates a magnetic field by means of coils 13. The amplitudes of the different magnetic fields are measured through the object, the catheter 14 or a stent, and from these amplitudes the position of the catheter 14 is determined and/or its track followed. The magnetic locating system 12 can comprise its own separate reproduction device.

Figure 2:
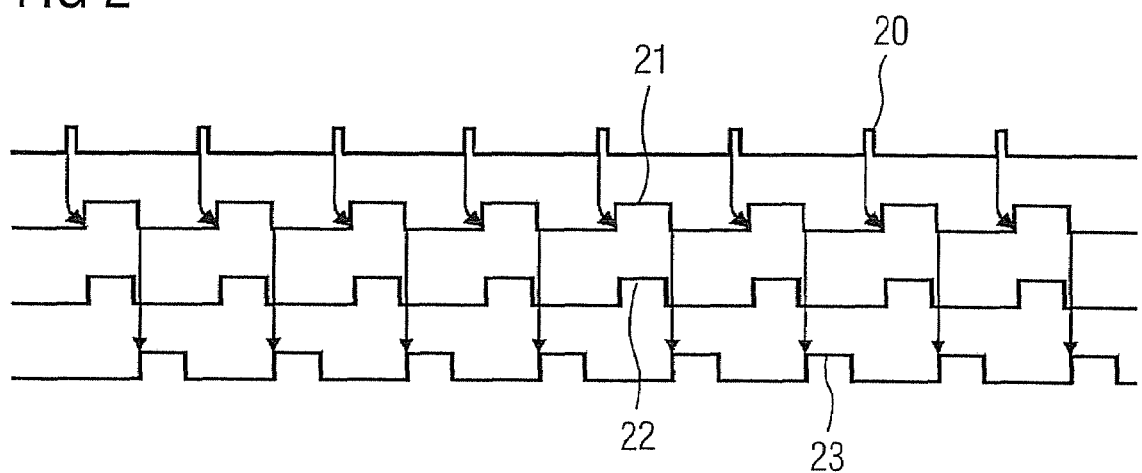
FIG. 2 shows a signal clock sequence of a known diagnostics device.

FIG. 2 accordingly shows the clock signals of a known X-ray image system 6. The video clock (frame request) 20 can, for example, have a frequency of 25 Hz or 30 Hz. This video clock 20 is sent by the X-ray image system 6 to the flat image detector 3. The latter subsequently sends an X-ray enabling signal (X-ray Enable) as a window 21 back to the X-ray image system 6. The X-ray image system 6 applies the X-rays 22 within this widow 21. The X-ray images 23 brought about by the X-rays 22 are read out, in a manner controlled by the electronic read-out device 5.

X-ray systems of this type used, for example, in cardiology provide a series of successive X-ray images. The X-ray images are conventionally taken and displayed at 30 Hz. Locating systems 12 for catheters 14 can operate at a plurality of fixed frequencies.

According to the invention the frequencies of the two systems should be coordinated with one another in a first step such that the interference is practically static from one X-ray image cycle to the next. This is the case for example if the frequencies of the locating system 12 for catheter 14, wherein a plurality of frequencies may be involved, are a multiple of the basic frequency of the X-ray system.

The X-ray image system 6 can, for example, operate at a frequency of 30 Hz, while the locating system 12 for catheter 14 can be operated at frequencies of for example 2,100 Hz, 2,190 Hz or 2,280 Hz, etc.

Therefore, the frequencies of the two systems must be coordinated with each other as precisely as possible. It is immaterial which of the two systems is adjusted in this case.

"Static" image interference, or image interference which moves only very slowly from one image to the next, is obtained as a result. If dark images are occasionally now taken during the X-ray image series, which images also contain this interference, this dark image can be used for correction for the subsequent exposed images.

For this reason the X-ray image system 6 according to the invention accordingly comprises an image memory 17 and a subtraction stage 18 as the correcting device. The control device 9 is also provided with adjusting means 19 for changing and adjusting the operating frequencies of the image system 6. These can be manual adjusting means 19 by way of which the operating frequencies of the X-ray system 1 to 11 may be adjusted via selector switches or dials. However, by way of example this may also take place via a keyboard (not shown) by means of which the frequencies may, for example, be directly input as numerical values.

Therefore, the frequencies of the two systems 1 to 12 are firstly coordinated with one another such that the interference no longer runs through the image. This occurs in particular if the operating frequency of the magnetic locating system 12 for objects 14 is an integral multiple of the operating frequency of the X-ray image system 6. If the magnetic locating system 12 comprises a plurality of operating frequencies, it is expedient if the differences in the operating frequencies are an integral multiple of the operating frequency of the X-ray image system 6. In the case of operating frequencies of the locating system this can, for example, lead to the operating frequency of the X-ray system 1 to 11 being reduced to 28,571 Hz or increased to 33,333 Hz in 200 Hz increments.

Figure 3:
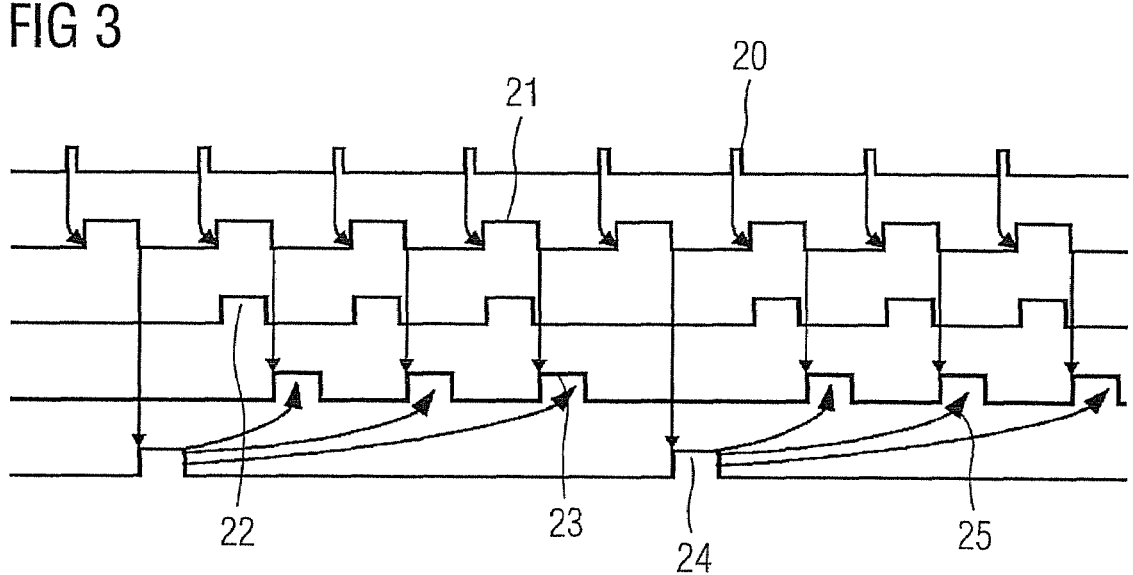
FIG. 3 shows a signal clock sequence of a diagnostics device according to the invention.

The further mode of operation of the X-ray image system 6 according to the invention will now be described in more detail with reference to FIG. 3. If a dark image is to be captured, the window 21 of the X-ray enable signal from the flat image detector 3 is nevertheless returned to the X-ray image system 6 but the X-ray image system 6 will decide not to apply any X-rays. Instead, owing to the video signal 20, a dark image is stored in the image memory 17 as a correction image 24 from the flat image detector 3 by means of the electronic read-out devices. Pulsed fluoroscopy then takes place, as a result of which a plurality of X-ray images 23, three in the illustrated example, is produced. A dark scan then takes place again, which is stored in the image memory 17 as the next correction image 24.

The X-ray images 23 are corrected on the basis of these correction images 24, which are read-out from the image memory 17, by the correction device 18, for example by means of subtraction in the correction device 18, as is indicated by the arrow 25.

Instead of changing and adjusting the operating frequencies of the image system via the adjusting means 19 they may also be associated with the locating system 12.

As an alternative to alternating capture of correction images 24 during a series, offsetting or determining of the correcting image 24 may also be carried out in what is known as the "Offset UpDate" which is usually performed in the irradiation pauses or during initialization of the detector. This is possible if the frequencies of the two systems are perfectly coordinated with one another. For this purpose, the control device 9 is also connected via a control line 16 to the magnetic locating system 12 for synchronization.

The advantage is that the X-ray system 1 to 11 and the locating system 12 for catheter 14 can simultaneously be operated without reciprocal influence—an imperative requirement of the clinical procedure.

It is also possible to operate modern flat image detector technology in connection with locating systems 12 for catheter 14 if the frequencies of the two systems can be sufficiently coordinated with one another. Recourse to image intensifier systems, which will soon no longer be available, is thus not necessary.

The invention claimed is:

1. A diagnostics device, comprising:
   an X-ray system that records sequential X-ray images having an image frequency, the X-ray system comprising an X-ray device and an imaging system assigned to the X-ray device;
   a locating system that locates objects, the locating system having an operating frequency;
   an adjusting unit that adjusts the image frequency or the operating frequency to match the X-ray system to the locating system such that interferences present in the sequential X-ray images are essentially static; and
   a correcting unit that eliminates the static interferences.

2. The diagnostics device according to claim 1, wherein the objects include a catheter or a medical instrument inserted into a body during a medical examination.

3. The diagnostics device according to claim 1, further comprising a control device for controlling the X-ray system or the locating system, wherein the control device includes the adjusting unit.

4. The diagnostics device according to claim 1, further comprising a subtracting unit, wherein the correcting unit comprises an image memory for storing a correction image.

5. The diagnostics device according to claim 4, wherein the correction image and X-ray images recorded after the correction image are fed to the subtracting unit.

6. The diagnostics device according to claim 1, wherein the adjusting unit includes the locating system.

7. The diagnostics device according to claim 1, wherein the image frequency is 30 Hz.

8. The diagnostics device according to claim 1, wherein the operating frequency is a multiple of 30 Hz.

9. The diagnostics device according to claim 1, wherein the image frequency is an integer factor of the operating frequency.

10. The diagnostics device according to claim 1, wherein the locating system is configured to be operated at a plurality of discrete frequencies spaced apart by 200 Hz.

11. A method of operating a diagnostics device, the diagnostics device comprising:
    an X-ray system for generating image signals related to sequential X-ray images and having an image frequency; and
    a locating system for locating objects, the locating system operating at an operating frequency, the method comprising:
    adjusting the image frequency or adjusting the operating frequency to match the X-ray system to the locating system such that interferences present in the sequential X-ray images are essentially static; and
    correcting the image signals relative to an optimization criterion such that the static interferences are minimized.

12. The method according to claim 11, further comprising:
    generating a correction image; and
    correcting the image signals related to X-ray images recorded after generating the correction image based on the correction image.

13. The method according to claim 12, wherein correcting the image signals related to X-ray images recorded after generating the correction image includes subtracting the correction image from the X-ray images recorded after generating the correction image.

14. The method according to claim 13, wherein the correction image is generated at the beginning of an examination and is subtracted from such X-ray images recorded during the examination.

15. The method according to claim 13, wherein a plurality of correction images is generated, each correction image created after recording a prescribable number of X-ray images.

16. The method according to claim 11, wherein the operating frequency is an integer multiple of the image frequency.

17. The method according to claim 11, further comprising configuring the locating system for operation at a plurality of discrete frequencies, where a difference between the discrete frequencies is an integer multiple of the image frequency.

* * * * *